(12) United States Patent
Trent et al.

(10) Patent No.: US 8,183,399 B2
(45) Date of Patent: May 22, 2012

(54) INTEGRATED HYDRO-OXIDATION PROCESS WITH SEPARATION OF AN OLEFIN OXIDE PRODUCT STREAM

(75) Inventors: David Trent, Katy, TX (US); Katherine Pividal, Baton Rouge, LA (US); Jon Siddall, Billerica, MA (US); Lanny Robbins, Midland, MI (US)

(73) Assignee: Dow Global Technologies LLC

( * ) Notice: Subject to any disclaimer, the term of this patent is extended or adjusted under 35 U.S.C. 154(b) by 452 days.

(21) Appl. No.: 12/530,874

(22) PCT Filed: Mar. 26, 2008

(86) PCT No.: PCT/US2008/058165
§ 371 (c)(1),
(2), (4) Date: Nov. 13, 2009

(87) PCT Pub. No.: WO2008/124292
PCT Pub. Date: Oct. 16, 2008

(65) Prior Publication Data
US 2010/0094031 A1    Apr. 15, 2010

Related U.S. Application Data

(60) Provisional application No. 60/921,947, filed on Apr. 5, 2007.

(51) Int. Cl.
*C07D 301/08* (2006.01)
*C07D 301/10* (2006.01)
*C07D 301/12* (2006.01)

(52) U.S. Cl. .................. 549/523; 549/534; 549/536

(58) Field of Classification Search .................. 549/523, 549/534, 536
See application file for complete search history.

(56) References Cited

U.S. PATENT DOCUMENTS

| | | | |
|---|---|---|---|
| 4,221,727 A | 9/1980 | Tsang et al. | |
| 4,990,632 A | 2/1991 | Ramachandran et al. | |
| 5,254,280 A | 10/1993 | Thomas et al. | |
| 5,532,384 A | 7/1996 | Shirley et al. | |
| 5,623,090 A | 4/1997 | Haruta et al. | |
| 5,859,265 A | 1/1999 | Muller et al. | |
| 6,008,389 A | 12/1999 | Grosch et al. | |
| 6,255,499 B1 | 7/2001 | Kuperman et al. | |
| 6,765,101 B1 | 7/2004 | Bhasin et al. | |
| 6,833,057 B1 | 12/2004 | Bessling et al. | |
| 7,279,451 B2 | 10/2007 | Singh et al. | |
| 2002/0052290 A1 | 5/2002 | Bowman et al. | |
| 2002/0161250 A1 | 10/2002 | Bowman et al. | |
| 2003/0031624 A1 | 2/2003 | Schummer et al. | |
| 2003/0144141 A1 | 7/2003 | Bowman et al. | |
| 2005/0103617 A1 | 5/2005 | Andreis et al. | |

FOREIGN PATENT DOCUMENTS

| | | |
|---|---|---|
| DE | 19600708 | 7/1997 |
| EP | 1293505 | 12/1987 |
| WO | 03062196 | 7/2003 |

OTHER PUBLICATIONS

Donohoe, A Metathesis-Based Approach to the Synthesis of Furans, Organic Letters, 2007, vol. 9, p. 953-956.
Gajewski, Energetic and Rate Effects of the Trifluoromethyl Group at C-2 and C-4 on the Aliphatic Claisen Rearrangement, Journal of Organic Chemicals, 1989, vol. 55, p. 1813.
Henne, Fluorinated Ethers, Journal of American Chemical Society, 1950, vol. 72, p. 4378.
Murata, Selective synthesis of fluorinated ethers by addition reaction of alcohols to fluorinated olefins in water, Green Chemistry, 2002, vol. 4, p. 60.

*Primary Examiner* — Bernard Dentz

(57) ABSTRACT

An integrated process providing for a gas phase hydro-oxidation of an olefin, preferably, propylene, with oxygen in the presence of hydrogen and a catalyst under reaction conditions such as to form a gaseous hydro-oxidation effluent stream containing an olefin oxide product, preferably, propylene oxide, water, unconverted olefin, oxygen, and hydrogen; and further providing for separation and recovery of the olefin oxide product from the effluent stream. The separation involves feeding the hydro-oxidation effluent stream into a first distillation column employing a liquid reflux rectification agent to obtain a first overhead stream containing unconverted olefin, oxygen, and hydrogen, which is recycled to the hydro-oxidation reactor, and a first bottoms stream containing water and the olefin oxide, from which upon further separation a purified olefin oxide product is recovered.

20 Claims, 2 Drawing Sheets

INTEGRATED HYDRO-OXIDATION PROCESS WITH SEPARATION OF AN OLEFIN OXIDE PRODUCT STREAM

CROSS REFERENCE TO RELATED APPLICATIONS

This application is a 371 of PCT/US2008/058165 filed Mar. 26, 2008, which claims the benefit of U.S. Provisional Application Ser. No. 60/921,947, filed Apr. 5, 2007.

BACKGROUND OF THE INVENTION

This invention pertains to an integrated process for hydro-oxidizing an olefin with oxygen in the presence of hydrogen to form an effluent stream comprising an olefin oxide, water, unconverted olefin, oxygen, and hydrogen and subsequently separating the effluent stream to obtain therefrom an olefin oxide product.

Olefin oxides, such as propylene oxide, are used to alkoxylate alcohols to form polyether polyols, which find widespread utility in the manufacture of polyurethanes and synthetic elastomers. Olefin oxides are also important intermediates in the manufacture of alkylene glycols, such as propylene glycol, and alkanolamines, such as isopropanolamine, which are useful as solvents and surfactants.

In past years several patents have disclosed gas and liquid phase processes for the direct hydro-oxidation of olefins having three or more carbon atoms (C3+) with oxygen in the presence of hydrogen to form corresponding olefin oxides. Catalysts for such processes are disclosed to comprise gold, silver, noble metals, such as palladium and platinum, or mixtures thereof, and optionally one or more promoters, such as alkali, alkaline earth, and rare earth elements, deposited on a titanium-containing support, such as, titania or a porous titanosilicate. Representative patents disclosing such hydro-oxidation processes include the following: EP-A1-0709360, WO 98/00413, WO 98/00414, WO 98/00415, U.S. Pat. No. 6,255,499, WO 03/062196, WO 96/02323, WO 97/25143, and WO 97/47386.

In gas phase hydro-oxidation processes, a gaseous effluent stream obtained from a hydro-oxidation reactor and comprising olefin oxide, water, and unconverted olefin, oxygen, and hydrogen is typically fed to a quench tower or column containing a liquid absorbent or solid adsorbent, wherein the olefin oxide is selectively removed from the effluent stream. Representative art disclosing the aforementioned separation methods include U.S. Pat. No. 4,990,632, U.S. Pat. No. 5,532,384, and US 2003/0031624 A1.

If a liquid absorbent is employed, the resulting liquid stream containing the olefin oxide dissolved in the absorbent is typically fed to a stripper column to recover a crude olefin oxide product. In this method, typically, a large quantity of absorbent is required; the olefin oxide is considerably diluted; and as a consequence, the absorbent and stripper columns are generally designed to handle a large quantity of liquid. Also, the stripper column may require a large energy input to meet the energy requirements for separating the olefin oxide from the absorbent. An unacceptably large temperature cycle may result between the absorbent column and the stripper column, between heating the olefin oxide-absorbent mixture in the stripper column and subsequently cooling the absorbent for recycle to the absorbent column. Moreover, the stripper column usually separates a crude olefin oxide product from the bulk absorbent, thereby necessitating a third distillation for recovery of a purified olefin oxide.

If the solid adsorbent method is employed, the process is cyclic rather than continuous, because the adsorbed olefin oxide must be desorbed from the column in a separate step. Moreover, at some point the adsorbent becomes saturated with the olefin oxide and needs to be regenerated. The solid adsorbent method can be facilitated by the use of two or more adsorbent columns operated in alternating cycles of adsorption and desorption; but such a multi-column method increases capital investment and operating costs.

Neither the liquid absorbent nor solid adsorbent method is completely satisfactory for commercialization. In view of the above, the art would benefit from integrating the gas phase hydro-oxidation process with an improved product separation method. Beneficially, such a process should operate continuously rather than intermittently; should avoid unacceptable dilution of the olefin oxide product; should lower energy demands and reduce temperature cycling; and should reduce to the extent possible capital investment and operating costs.

SUMMARY OF THE INVENTION

This invention provides for an integrated process of hydro-oxidizing an olefin to form a hydro-oxidation effluent stream comprising an olefin oxide product combined with a process of separating the effluent stream to recover the olefin oxide product. The process of this invention comprises the steps of:

(a) contacting a reactant olefin in a hydro-oxidation reactor in a gas phase with oxygen in the presence of hydrogen and in the presence of a hydro-oxidation catalyst under reaction conditions sufficient to obtain a gas phase hydro-oxidation effluent stream comprising an olefin oxide, water, unconverted olefin, oxygen, and hydrogen;

(b) feeding the gas phase hydro-oxidation effluent stream into a first distillation column that provides for a liquid reflux of a rectification agent in the top one-third (⅓) section of the column;

(c) removing from the first distillation column a first overhead stream comprising unconverted olefin, oxygen, and hydrogen, and a first bottoms stream comprising water and the olefin oxide; and (d) feeding the stream comprising water and the olefin oxide into a finishing train to obtain therefrom a stream consisting essentially of the olefin oxide product.

The aforementioned invention provides for an integrated process for the gas phase hydro-oxidation of an olefin with oxygen in the presence of hydrogen to produce an effluent stream comprising an olefin oxide, water, and unconverted reactants, including unconverted olefin, oxygen, and hydrogen, combined with an improved separation of the hydro-oxidation effluent stream to obtain the olefin oxide product. Advantageously, all process steps can be operated continuously for optimal productivity. In addition, the separation step of this invention beneficially avoids unacceptable dilution of the olefin oxide with a liquid absorbent; avoids recovery of a liquid absorbent; and avoids any temperature cycling associated with use of a liquid absorbent. Moreover, the separation stage of this invention calls for a lower energy input and reduced capital investment and operating costs, as compared with the liquid absorbent and solid adsorbent separation methods of the prior art.

DETAILED DESCRIPTION OF THE INVENTION

Figure 1:
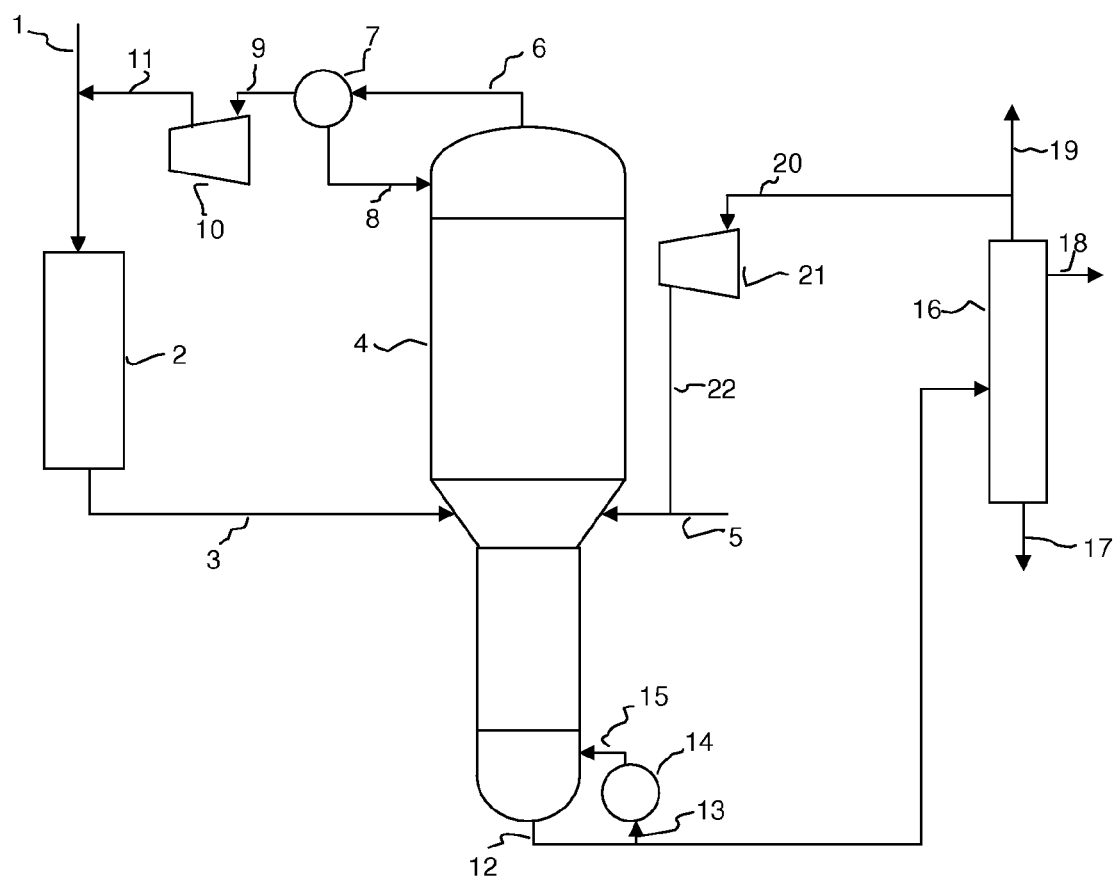
FIG. 1 depicts a first preferred embodiment of this invention comprising a gas phase hydro-oxidation process for reacting an olefin with oxygen in the presence of hydrogen and a hydro-oxidation catalyst to form a gaseous effluent stream comprising an olefin oxide, water, unconverted olefin, oxygen, and hydrogen; a distillation stage to recover a bottoms stream comprising water and the olefin oxide product; and a finishing stage to recover a purified olefin oxide product.

As summarized hereinabove, this invention provides for an integrated process for the hydro-oxidation of an olefin to form a hydro-oxidation effluent stream comprising an olefin oxide, combined with an improved process of separating the olefin oxide from the hydro-oxidation effluent stream. The process of this invention comprises the steps of:

(a) contacting a reactant olefin in a hydro-oxidation reactor in a gas phase with oxygen in the presence of hydrogen and in the presence of a hydro-oxidation catalyst under reaction conditions sufficient to obtain a gas phase hydro-oxidation effluent stream comprising an olefin oxide, water, unconverted olefin, oxygen, and hydrogen;

(b) feeding the gas phase hydro-oxidation effluent stream into a first distillation column that provides for a liquid reflux of a rectification agent in the top one-third ($\frac{1}{3}$) section of the column;

(c) removing from the first distillation column a first overhead stream comprising unconverted olefin, oxygen, and hydrogen, and a first bottoms stream comprising water and the olefin oxide; and (d) feeding the stream comprising water and the olefin oxide into a finishing train to obtain therefrom a stream comprising the olefin oxide product.

In a preferred embodiment of this invention, the olefin is propylene and the olefin oxide is propylene oxide.

In another preferred embodiment of this invention, the rectification agent comprises an aliphatic hydrocarbon having a normal boiling point equal to or greater than the normal boiling point of the olefin and less than the normal boiling point of the olefin oxide. Preferably, the rectification agent is the same olefin as is used in the hydro-oxidation process, more preferably, propylene. Alternatively, the rectification agent is a $C_{4-8}$ alkane, more preferably, butane or isobutane.

In another preferred embodiment of this invention, the hydro-oxidation catalyst comprises gold, silver, a noble metal, such as palladium or platinum, a rare earth lanthanide, or a mixture thereof deposited on a titanium-containing support. In a more preferred embodiment, the titanium-containing support comprises a porous titanosilicate.

In another preferred embodiment, the hydro-oxidation catalyst, comprising gold, silver, a noble metal, a rare earth lanthanide, or a mixture thereof deposited on the titanium-containing support, further comprises a promoter selected from the group consisting of alkali, alkaline earths, rare earth lanthanides, actinide elements, and mixtures thereof. Notably, the rare earth lanthanides may function as the catalytic metal or promoter depending upon the specific form of the other components in the catalyst. Specifically, when the catalyst comprises gold, silver, and/or any other noble metal, the rare earth lanthanides are generally considered to act as promoters. When gold, silver, and/or other noble metals are absent, the rare earth lanthanides are generally considered to perform as the primary catalytic metal.

In a first preferred embodiment, the process of this invention comprises the steps of:

(a) contacting a reactant olefin in a hydro-oxidation reactor in a gas phase with oxygen in the presence of hydrogen and in the presence of a hydro-oxidation catalyst under reaction conditions sufficient to obtain a gas phase hydro-oxidation effluent stream comprising an olefin oxide, water, unconverted olefin, oxygen, and hydrogen;

(b) feeding the gas phase hydro-oxidation effluent stream into a bottom one-third ($\frac{1}{3}$) section of a first distillation column that provides for a liquid reflux of the olefin in a top $\frac{1}{3}$ section of the column;

(c) removing from the first distillation column a first overhead stream comprising unconverted olefin, oxygen, and hydrogen, and a first bottoms stream comprising water and the olefin oxide;

(d) feeding the first overhead stream into a condenser and withdrawing therefrom a gaseous stream comprising oxygen, hydrogen, and a portion of the unconverted olefin, and a liquid stream comprising the balance of the unconverted olefin;

(e) recycling the gaseous stream comprising oxygen, hydrogen, and a portion of the unconverted olefin obtained from the condenser to the hydro-oxidation reactor;

(f) recycling the liquid stream comprising the balance of the unconverted olefin obtained from the condenser to the top $\frac{1}{3}$ section of the distillation column to provide for the liquid reflux;

(g) feeding at least a portion of the bottoms stream from the first distillation column into a finishing train to obtain therefrom a second overhead stream comprising the olefin oxide.

With respect to the aforementioned first preferred embodiment, optionally, additional reactant olefin may be fed to the first distillation column, preferably, the middle $\frac{1}{3}$ section of the first distillation column, to make-up or increase the olefin liquid reflux. As a further option, a portion of the first bottoms stream comprising the olefin oxide and water may be fed to a reboiler from which any unconverted olefin present in the first bottoms stream is separated and recycled to the first distillation column.

More specifically, with reference to FIG. 1, a gaseous reactant feedstream (1) comprising olefin, oxygen, and hydrogen, described hereinafter, is fed to a hydro-oxidation reactor (2) containing the hydro-oxidation catalyst. Exiting from the hydro-oxidation reactor (2) is gaseous effluent stream (3) comprising olefin oxide, water, unconverted olefin, oxygen, and hydrogen, which is fed to a first distillation column (4). Also fed to the first distillation column via feedstream input line (5) is additional reactant olefin. Exiting from the first distillation column (4) is first overhead stream (6) comprising unconverted olefin, oxygen, and hydrogen, which is fed to condenser (7) for condensation of at least a portion of the unconverted olefin. Effluent stream (8) obtained from the condenser (7) comprising the condensed portion of the unconverted olefin is recycled to the first distillation column (4) to provide for an olefin liquid reflux in the top $\frac{1}{3}$ section of the first distillation column. In this embodiment of the invention, the rectification agent is the identical olefin as is used in the hydro-oxidation process. Effluent stream (9) obtained from condenser (7) comprising the uncondensed remainder of the unconverted olefin, oxygen, and hydrogen is fed to compressor (10) from which resulting compressed feedstream (11) is fed into reactant feedstream (1) for recycle to the hydro-oxidation reactor (2).

From first distillation column (4) is also obtained a first bottoms stream (12) comprising water and the olefin oxide product, a portion of which may be fed via feed line (13) to reboiler (14) from which is obtained effluent stream (15) comprising any olefin that may be present in the first bottoms stream, which effluent stream (15) is recycled to the first distillation column (4). The remainder of first bottoms stream (12) is fed to a finishing train, which may be one or more distillation columns, e.g., (16), from which a second bottoms stream (17) comprising water is obtained. The water is typically disposed. Also, obtained from second distillation column (16) is stream (18) comprising propylene oxide product. Effluent stream (19) comprising residual gases, including unconverted olefin, oxygen, and/or hydrogen may be obtained from the top of finishing column (16). All or a portion of the top stream (19) can be fed via line (20) to compressor (21), and from compressor (21) fed via effluent line (22) into feedstream (5) for recycle to the first distillation column (4). Any remainder of the top stream (19) not recycled is typically vented.

In a second preferred embodiment, the process of this invention comprises the steps of:

(a) contacting in a gas phase in a hydro-oxidation reactor a reactant olefin with oxygen in the presence of hydrogen and in the presence of a hydro-oxidation catalyst under reaction conditions sufficient to obtain a gaseous hydro-oxidation effluent stream comprising an olefin oxide, water, unconverted olefin, oxygen, and hydrogen;

(b) feeding the gas phase hydro-oxidation effluent stream into a first distillation column which provides for a liquid reflux of an alkane in the upper ⅓ section of the column;

(c) removing from the first distillation column a first overhead stream comprising unconverted olefin, oxygen, hydrogen, and a portion of the alkane, and a first bottoms stream comprising water, olefin oxide, and the balance of the alkane;

(d) feeding the first overhead stream to a condenser and obtaining therefrom a gaseous stream comprising unconverted olefin, oxygen, hydrogen, and a portion of the alkane fed to the condenser and a liquid stream comprising the balance of the alkane fed to the condenser;

(e) recycling the gaseous stream obtained from the condenser to the hydro-oxidation reactor;

(f) recycling the liquid stream obtained from the condenser to the top ⅓ section of the first distillation column;

(g) feeding the first bottoms stream comprising water, olefin oxide, and the balance of the alkane from the first distillation column to a stripper column to obtain a second overhead stream comprising the alkane and a second bottoms stream comprising water and the olefin oxide;

(h) recycling the second overhead stream comprising the alkane to the hydro-oxidation reactor and/or the first distillation column; and (i) feeding the second bottoms stream comprising water and the olefin oxide to a finishing train to obtain therefrom a third overhead stream comprising the olefin oxide product.

With respect to the aforementioned second preferred embodiment, optionally, the reactant olefin can be additionally fed to the first distillation column, preferably, the middle ⅓ section of the first distillation column, for make-up olefin; and the alkane can be additionally fed to the first distillation column, preferably, the top and/or middle ⅓ section of the first distillation column, for make-up liquid reflux. As a further option, a portion of the first bottoms stream comprising the olefin oxide, water, and the alkane may be fed to a reboiler from which the alkane and any unconverted olefin present in the first bottoms stream is separated and recycled to the first distillation column.

Figure 2:
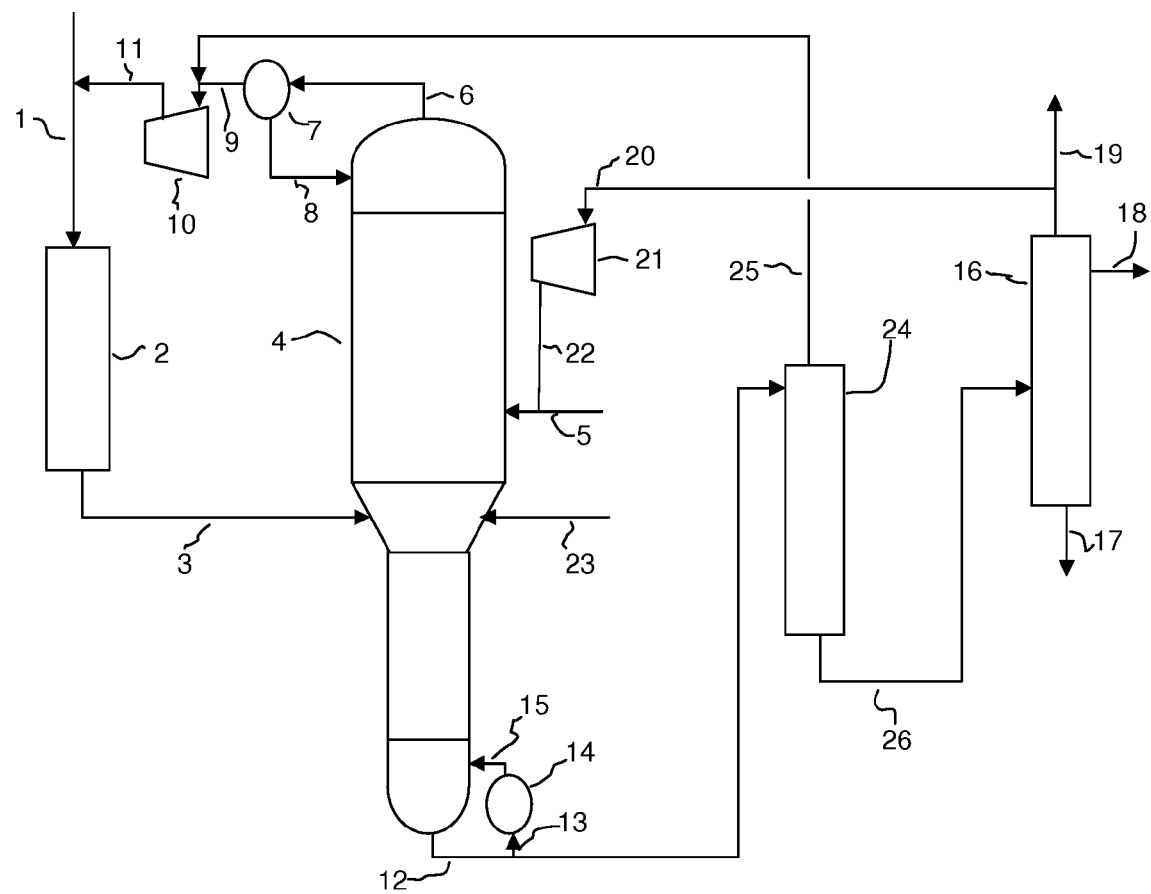
FIG. 2 depicts a second preferred embodiment of this invention comprising a gas phase hydro-oxidation process for reacting an olefin with oxygen in the presence of hydrogen and a hydro-oxidation catalyst to form a gaseous effluent stream comprising an olefin oxide, water, unconverted olefin, oxygen, and hydrogen; a distillation stage to recover a bottoms stream comprising water, the olefin oxide product, and an alkane rectification agent; a stripper stage to separate water and the olefin oxide from the alkane rectification agent; and a finishing stage to recover a purified olefin oxide product.

With reference to FIG. 2 illustrating the aforementioned preferred embodiment, a gaseous reactant feedstream (1) comprising olefin, oxygen, and hydrogen is fed to a hydro-oxidation reactor (2) containing the hydro-oxidation catalyst. Exiting from the hydro-oxidation reactor (2) is gaseous effluent stream (3) comprising olefin oxide, water, unconverted olefin, oxygen, and hydrogen, which is fed to a first distillation column (4). Optionally, additional reactant olefin may be fed to the first distillation column via feed line (5). Also fed to the first distillation column via feed line (23) is an aliphatic hydrocarbon rectification agent, in this instance an alkane. Exiting from the first distillation column (4), first overhead stream (6) comprises unconverted olefin, oxygen, hydrogen, and a portion of the alkane, which stream (6) is fed to condenser (7) for condensation of a portion of the alkane fed to the condenser. Liquid stream (8) obtained from condenser (7) comprising primarily liquid alkane is recycled to the first distillation column (4) to provide for a liquid reflux in the top ⅓ section of the column. Gaseous effluent stream (9) obtained from the condenser (7) comprising the unconverted olefin, oxygen, hydrogen, and alkane is fed to compressor (10), from which compressed stream (11) is obtained and fed into stream (1) for recycle to the hydro-oxidation reactor (2).

From first distillation column (4) is also obtained a first bottoms stream (12) comprising water, the olefin oxide product, and the remaining portion of the alkane. The first bottoms stream (12) is fed to stripper column (24) from which is obtained a second overhead stream (25) comprising the alkane, which is recycled to stream (9) and/or to stream (23), and a second bottoms stream (26) comprising water and the olefin oxide. Stream (26) is fed to a finishing train (16) from which a water stream (17) and a purified propylene oxide product (18) are obtained. Effluent stream (19) comprising residual gases, including any unconverted olefin, oxygen, and/or hydrogen may be obtained from the top of finishing column (16). All or a portion of the top stream (19) can be fed via line (20) to compressor (21), and from compressor (21) fed via effluent line (22) into feedstream (5) for recycle to the first distillation column (4). Any remainder of the top stream (19) not recycled is typically vented. It is also possible to take a portion of the first bottoms stream via feed line (13) to reboiler (14) from which is obtained effluent stream (15) comprising any residual alkane and olefin that are present in the first bottoms stream, which effluent stream (15) is recycled to the first distillation reactor (4).

Any mono-olefin having from 2 to about 5 carbon atoms is suitable for the process of this invention. The olefin can exclusively contain carbon and hydrogen atoms; or alternatively, the olefin can be substituted at any of the carbon atoms with an inert substituent. As used herein, the term "inert" refers to a substituent that is substantially non-reactive in the process of this invention. Suitable inert substituents include, but are not limited to halides, ether, ester, alcohol, and aromatic moieties; preferably, chloro, $C_{1-3}$ ether, $C_{1-3}$ ester, and $C_{1-3}$ alcohol moieties. Non-limiting examples of olefins that are suitable for the process of this invention include ethylene, propylene, 1-butene, 2-butene, isobutylene (2-methylpropene), 1-pentene, 2-pentene, 2-methyl-1-butene, 2-methyl-2-butene; as well as allyl alcohol, allyl ether, allyl ethyl ether, allyl butyrate, allyl acetate and allyl chloride. Preferably, the olefin is propylene.

The prior art adequately describes the molar ratios of olefin, oxygen, hydrogen, and any optional diluent suitable for the hydro-oxidation reaction as well as suitable reactors and process conditions, including temperature, pressure, and space velocities. Reference is made to WO 98/00413, WO 98/00414, WO 98/00415, U.S. Pat. No. 6,255,499, WO 03/062196, incorporated herein by reference. For sufficiency of description, suitable hydro-oxidation process conditions are summarized hereinafter.

Typically, the quantity of olefin is greater than about 1, preferably, greater than about 5, and more preferably, greater than about 10 mole percent, based on the total moles of olefin, oxygen, hydrogen, and optional diluent, the diluent being described hereinafter. Typically, the quantity of olefin is less than about 99, and preferably, less than about 80, and more preferably, less than about 60 mole percent, based on the total moles of olefin, oxygen, hydrogen, and optional diluent.

Any source of oxygen is acceptable for the hydro-oxidation step, including air or substantially pure molecular oxygen. Molecular oxygen is preferred. The quantity of oxygen employed can vary over a wide range as described in the art. Preferably, the quantity of oxygen is greater than about 0.01, more preferably, greater than about 1, and most preferably greater than about 5 mole percent, based on the total moles of olefin, oxygen, hydrogen, and optional diluent. Preferably, the quantity of oxygen is less than about 30, more preferably, less than about 25, and most preferably less than about 20 mole percent, based on the total moles of olefin, oxygen, hydrogen, and optional diluent. Above about 20 mole percent, the concentration of oxygen may fall within the flammable range for olefin-hydrogen-oxygen mixtures.

Any source of hydrogen can be fed to the hydro-oxidation step including, for example, molecular hydrogen obtained from the dehydrogenation of hydrocarbons and alcohols, or hydrogen generated in situ in the olefin oxidation reactor, for example, by dehydrogenating alkanes, such as propane or isobutane, or alcohols, such as isobutanol. The trace quantity of hydrogen in air is too negligible to provide the necessary quantity of hydrogen to the process of this invention. A source of additional hydrogen must be fed to the process or generated in situ in the process. Suitable quantities of hydrogen are typically greater than about 0.01, preferably, greater than about 0.1, and more preferably, greater than about 3 mole percent, based on the total moles of olefin, oxygen, hydrogen, and optional diluent. Suitable quantities of hydrogen are typically less than about 50, preferably, less than about 30, and more preferably, less than about 20 mole percent, based on the total moles of olefin, oxygen, hydrogen, and optional diluent.

Optionally, it may be desirable to employ in the hydro-oxidation process a gaseous diluent, which beneficially provides a means of removing and dissipating the exotherm of the reaction. In addition, the diluent provides an expanded concentration regime in which the reactants are non-flammable. Suitable gaseous diluents include, but are not limited to helium, nitrogen, argon, methane, carbon dioxide, steam, and mixtures thereof. The amount of diluent is typically greater than about 0, preferably greater than about 0.1, and more preferably, greater than about 15 mole percent, based on the total moles of olefin, oxygen, hydrogen, and diluent. The amount of diluent is typically less than about 90, preferably, less than about 80, and more preferably, less than about 70 mole percent, based on the total moles of olefin, oxygen, hydrogen, and diluent.

The catalyst employed in the hydro-oxidation stage of this invention is well known in the art as described, for example, in EP-A1-0709360, WO 98/00413, WO 98/00414, WO 98/00415, U.S. Pat. No. 6,255,499, WO 03/062196, WO 96/02323, WO 97/25143, and WO 97/47386, incorporated herein by reference. Preferably, the hydro-oxidation catalyst comprises gold, silver, one or more noble metals, one or more rare earth lanthanides, or a mixture thereof, deposited on a titanium-containing support. The noble metals include ruthenium, rhodium, palladium, osmium, iridium, and platinum, preferably, palladium and/or platinum. The rare earth lanthanides include lanthanum, cerium, praseodymium, neodymium, promethium, samarium, europium, gadolinium, terbium, dysprosium, holmium, thulium, ytterbium, and lutetium, preferably, lanthanum, erbium, lutetium, or a mixture thereof. A most preferred catalytic metal comprises gold alone or comprises both gold and silver, in either instance, optionally, comprising one or more noble metals or lanthanide rare earths. As disclosed in the art, the total loading of catalytic metal (i.e., gold, silver, noble metals, and/or lanthanides), is typically greater than about 0.001 weight percent (10 parts per million, ppm) and typically less than about 20 weight percent, based on the total weight of the catalyst.

The titanium-containing support may comprise any such support known to be operative in hydro-oxidation processes, for example, titania, titania-silica, titanosilicate, titanium dispersed on silica or alumina, titanium dispersed on a promoter metal silicate (wherein promoter metals are defined hereinafter), promoter metal titanates, as well as mixtures of the aforementioned supports. In a more preferred embodiment, the titanium-containing support comprises a porous titanosilicate, most preferably, a microporous crystalline titanosilicate of MFI crystallographic structure.

Optionally, the hydro-oxidation catalyst further comprises one or more promoters selected from the group consisting of alkali, alkaline earths, rare earth lanthanides, actinides, and mixtures thereof. Preferably, the promoter is selected from the group consisting of lithium, sodium, potassium, rubidium, cesium, magnesium, calcium, barium, erbium, lutetium, and mixtures thereof. As disclosed in the art, the total loading of promoter(s) is typically greater than about 0.001 weight percent (10 parts per million, ppm) and typically less than about 20 weight percent, based on the total weight of the catalyst.

The hydro-oxidation step can be conducted in a reactor of any conventional design capable of handling an exothermic gas phase process. Preferred reactor designs include fixed-bed, shell and tube, fluidized bed, and moving bed reactors, as well as swing reactors constructed from a plurality of catalyst beds connected in parallel and used in an alternating fashion.

The process conditions for the hydro-oxidation step can vary considerably over a nonflammable and flammable regime. It is beneficial to recognize the conditions that distinguish between nonflammable and flammable mixtures of the olefin, hydrogen, and oxygen, and optional diluent. Accordingly, a composition diagram can be constructed or consulted showing the flammable and non-flammable range of reactant compositions at the desired operating temperature and pressure. The more preferred reactant mixtures specified hereinabove are believed to lie outside the flammable regime when the process is operated at the more preferred temperatures and pressures specified hereinbelow. Nevertheless, operation within the flammable regime is possible, as designed by one skilled in the art.

Usually, the hydro-oxidation step is conducted at a temperature that is greater than about 140° C., preferably, greater than about 160° C. Usually, the hydro-oxidation step is conducted at a temperature less than about 300° C., preferably less than about 280° C. Usually, the pressure ranges from about atmospheric to about 500 psia (3,448 kPa), preferably, from about 100 psia (690 kPa) to about 300 psia (2,069 kPa). The gas hourly space velocity (GHSV) of the olefin can vary over a wide range, but typically is greater than about 10 ml olefin per ml catalyst per hour ($h^{-1}$), preferably greater than about 100 $h^{-1}$, and more preferably, greater than about 1,000 $h^{-1}$. Typically, the GHSV of the olefin is less than about 50,000 $h^{-1}$, preferably, less than about 35,000 $h^{-1}$, and more preferably, less than about 20,000 h$^{-1}$. The total gas hourly space velocity (GHSV) of the feedstream comprising olefin, oxygen, hydrogen, and optional diluent can also vary over a wide range, but typically is greater than about 10 ml gas per ml catalyst per hour (h$^{-1}$), preferably, greater than about 100 h$^{-1}$, and more preferably, greater than about 1,000 h$^{-1}$. Typically, the GHSV of the feedstream comprising olefin, oxygen, hydrogen, and optional diluent is less than about 50,000 h$^{-1}$, preferably, less than about 35,000 h$^{-1}$, and more preferably, less than about 20,000 h$^{-1}$. The gas hourly space velocities of the oxygen, hydrogen, and diluent components can be determined from the space velocity of the olefin taking into account the relative molar ratios desired.

The gaseous effluent stream leaving the hydro-oxidation reactor comprises olefin oxide, water (which is a co-product of the hydro-oxidation of the olefin, a by-product of olefin combustion, and a by-product of hydrogen combustion), unconverted reactant olefin, oxygen, hydrogen, optional diluent as may have been used, as well as oxidation by-products (e.g., propionaldehyde, carbon monoxide, and carbon dioxide). Typically, the concentration of olefin oxide in the effluent stream leaving the hydro-oxidation reactor is relatively dilute, ranging from greater than about 0.05 volume percent to less than about 10 volume percent, based on the total volume of the effluent stream. Typically, the concentration of water (steam) in the effluent stream from the hydro-oxidation reactor is greater than about 0.1 volume percent and less than about 15 volume percent, based on the total volume of the effluent stream. Typically, the concentration of unconverted olefin in the effluent stream from the hydro-oxidation reactor is greater than about 1 volume percent and less than about 80 volume percent, based on the total volume of the effluent stream. Typically, the concentration of oxygen in the effluent stream is greater than about 0.5 volume percent and less than about 20 volume percent, based on the total volume of the effluent stream. Typically, the concentration of hydrogen is greater than about 0.1 volume percent and less than about 20 volume percent, based on the total volume of the effluent stream. Typically, the diluent is employed in a concentration ranging from 0 to less than about 70 volume percent, based on the total volume of the effluent stream.

The gaseous effluent from the hydro-oxidation reactor is fed into the first distillation column at a point anywhere along the column from the bottom of the column up to the mid-point of the column, preferably, from the bottom of the column to a height of about ⅓ up from the bottom. Suitable distillation columns include trayed or packed columns, with packed columns being preferred. No limitation is placed on the type of packing, suitable examples of which include structured or dump packing made of metal or ceramic compatible with the chemicals and process conditions herein described. The skilled process engineer will be able to design the first distillation column to accommodate the specific vapor and liquid components employed and the desired vapor and liquid loadings. Typically, the theoretical number of plates in the first distillation column ranges from about 6 to about 50, preferably, from about 6 to about 20. The temperature at the bottom of the first distillation column, where the hydro-oxidation reactor effluent stream is fed, is typically greater than about 35° C., preferably, greater than about 45° C., but less than about 125° C., and preferably, less than about 100° C. The bottom pressure is typically greater than about 50 psia (345 kPa), preferably, greater than about 150 psia (1,034 kPa), and typically less than about 500 psia (3,446 kPa), and preferably, less than about 350 psia (2,412 kPa). The temperature at the top is determined by the condensation temperature of the reflux component at the operating pressure. The pressure of the first overhead stream leaving from the top of the first distillation column is desirably similar to the pressure within the hydro-oxidation reactor, so as to minimize compression requirements of the gaseous recycle to the hydro-oxidation reactor. Thus, the first overhead stream exits the distillation column at a pressure typically greater than about 50 psia (345 kPa), preferably, greater than about 150 psia (1,034 kPa), but typically less than about 500 psia (3,446 kPa), and preferably, less than about 350 psia (2,412 kPa).

The top ⅓ section of the first distillation column is required to contain a liquid reflux of a rectification agent. As used herein, the term "rectification agent" refers to a compound that facilitates the separation of components in a mixture during distillation. In this instance, the olefin oxide is relatively dilute in the gaseous hydro-oxidation effluent stream; and the rectification agent facilitates the separation of the olefin oxide therefrom. Preferably, the rectification agent is an aliphatic hydrocarbon having a normal boiling point equal to or greater than the normal boiling point of the olefin and less than the normal boiling point of the olefin oxide. The word "aliphatic hydrocarbon" refers to an organic compound containing exclusively carbon and hydrogen atoms, preferably in this instance, an alkane (i.e., hydrocarbon having each carbon atom therein covalently bonded to four atoms, that is, saturated) or an alkene (i.e., hydrocarbon containing at least one carbon=carbon unsaturated double bond). The term "normal boiling point" is defined herein as the temperature at which the liquid phase of a compound is in equilibrium with its vapor phase at a pressure of 1 atm (101 kPa). Non-limiting examples of suitable aliphatic hydrocarbon rectification agents include $C_{4-8}$ alkanes, such as butane, pentane, hexane, cyclohexane, heptane, and octane, and $C_{3-8}$ alkenes, such as propylene, butene, pentene, hexene, heptene, and octene, including all isomeric forms of the aforementioned alkanes and alkenes.

If an alkene is used as the rectification agent, it is clearly preferred to select the same olefin as the olefin reactant of the hydro-oxidation process, e.g., propylene in the preferred process, because any other alkene would be reactive in the hydro-oxidation process if recycled through the hydro-oxidation reactor, thereby complicating the overall process unnecessarily. If an alkane is chosen as the rectification agent, then it should be substantially inert with respect to the hydro-oxidation process. Under hydro-oxidation reaction conditions, alkanes are typically inert. Notably, an alkane having a normal boiling point that is higher than the normal boiling point of the hydro-oxidation reactant olefin will demand less energy (refrigeration/coolant) upon condensation, as compared with the olefin itself. For example, in the preferred process wherein the olefin is propylene, butane can be condensed with simply a water coolant, whereas propylene requires a refrigeration means. Consequently, it may be preferred from energy considerations to use the alkane, for example butane, as the rectification agent.

Any conventional design means that provides for the liquid reflux in the upper ⅓ section of the first distillation column is suitably employed. A preferred embodiment comprises an overhead condenser external to the distillation column with a conduit to deliver the resulting liquid phase rectification agent to the top ⅓ section of the first distillation column. Generally, the condenser is operated at a temperature sufficient to condense the rectification agent; thus the temperature depends upon the specific rectification agent employed and its liquefaction temperature at the operating pressure. Pressure is desirably maintained as close as operating conditions allow to the pressure in the hydro-oxidation reactor, which is typically greater than about 50 psia (345 kPa) and less than about 500 psia (3,446 kPa).

Any amount of rectification agent may be fed to the first distillation column provided that a sufficient liquid reflux is obtained to facilitate the separation of the olefin oxide from the hydro-oxidation effluent stream. The amount of rectification agent advantageously is sufficient to separate essentially all, i.e., greater than about 95 mole percent, preferably, greater than about 99 mole percent, of the olefin oxide to the bottom of the first distillation column. The skilled artisan knows how to determine a suitable amount of rectification agent to be fed to the first distillation column by taking into consideration parameters of the specific distillation employed. To effect this separation, a reflux ratio advantageously is employed that is greater than about 0.1/1 and less than about 10/1. Reflux ratio is defined as the weight ratio of liquid reflux in the column to forward flow from the column. Preferably, the reflux ratio is greater than about 0.1/1 and less than about 5/1, more preferably, less than about 1/1. The liquid reflux may be provided via a liquid stream obtained from the condenser or a make-up stream provided in a separate feed to the distillation column Safety precautions should be taken to ensure that the gaseous stream comprising unconverted olefin, oxygen, hydrogen, optional diluent, and alkane rectification agent, if any, exiting the condenser does not comprise a flammable mixture. The skilled process engineer will know how to determine what mixtures fall within the flammable and non-flammable ranges as noted hereinbefore.

A first bottoms stream comprising water, olefin oxide, and optionally residual unconverted olefin and/or rectification agent, such as an alkane, exits the bottom of the first distillation column. Typically, this first bottoms stream comprises from greater than about 50 to less than about 90 mole percent water, from greater than about 10 to less than about 50 mole percent olefin oxide, from greater than about 0 to less than about 1 mole percent unconverted olefin, and from about 0 to less than about 20 mole percent other rectification agent, such as, alkane. Optionally, a portion of the first bottoms stream may be sent to a reboiler of conventional design. The portion of the first bottoms stream sent to the reboiler can range from 0 to about 30 weight percent, based on the total weight of the first bottoms stream. If used, the reboiler is operated at a temperature and pressure sufficient to recover any unconverted olefin reactant and/or rectification agent that may be present in the first bottoms stream for recycle to the first distillation column.

If the reactant olefin, itself, is employed as the liquid reflux rectification agent, then the first bottoms stream comprising water and olefin oxide is fed, in whole or in part, to a finishing train of one or more distillation columns capable of separating the olefin oxide from water to the desired degree of product purity. Suitable designs include trayed and packed columns, with packing preferred, similar to those as noted hereinbefore. The first finishing column typically contains from about 10 to about 50 theoretical plates and is operated, preferably, at a temperature greater than about −30° C. and less than about 140° C. at a pressure ranging from about 8 psia (55 kPa) to about 60 psia (413 kPa). A second bottoms stream comprising water is obtained from the first finishing column; the water stream is typically disposed. A second overhead stream consisting substantially of olefin oxide, preferably propylene oxide, is obtained from the first finishing column. The olefin oxide product typically has a purity of greater than about 60 weight percent, preferably, greater than about 75 weight percent, and more preferably, greater than about 90 weight percent, based on the total weight of the olefin oxide stream. The olefin oxide product is suitable for sale or further purification, as desired.

If a rectification agent other than the olefin itself is used, for example, an alkane, then the first bottoms stream comprising water, olefin oxide, and rectification agent, is fed in whole or in part to a stripper column from which is obtained a second overhead stream comprising the rectification agent which is recycled to the first distillation column and/or the hydro-oxidation reactor. A second bottoms stream comprising water and propylene oxide is obtained from the stripper column. The stripper column is operated at any temperature and pressure sufficient to strip the rectification agent from the water and olefin oxide. In a preferred embodiment, wherein the first bottoms stream comprises water, propylene oxide, and butane, the stripper is operated typically at a temperature greater than about −30° C. and less than about 140° C. and a pressure greater than about 8 psia (55 kPa) and less than about 362 psia (2500 kPa). The second bottoms stream comprising water and the olefin oxide obtained from the stripper column is then fed into the finishing train as previously described herein. In this design a third bottoms stream comprising water and a third overhead stream consisting substantially of olefin oxide, preferably propylene oxide, is obtained from the finishing train.

The following examples are provided to illustrate the invention described herein; however, these examples should not be construed to limit the invention in any manner. Based on the description herein, the skilled artisan will be able to vary the parameters of the invention to produce a variety of embodiments that fall within the scope of the claims.

Example 1

With reference to FIG. 1 and Table 1, a catalyst (61,800 kg) comprising gold deposited on a microporous titanosilicate support is prepared in accordance with the description in U.S. Pat. No. 6,255,499 and then loaded into a fixed-bed, continuous flow reactor (137 m$^3$ volume). (FIG. 1, unit 2) The catalyst is employed in a hydro-oxidation of propylene with oxygen in the presence of hydrogen to form propylene oxide and co-product water. A flow of hydrogen (10 percent by volume in nitrogen) is started. The reactor is heated from room temperature to 250° C. at a rate of 120° C./hour, held at 250° C. for 1 hour, and then cooled to 100° C. The reactor is then fed with nitrogen, heated to 160° C., and held for 1 hour. Thereafter, the temperature is reduced to 140° C., and then a feed comprising propylene, oxygen, and hydrogen is introduced (FIG. 1, input stream 1) The process temperature is maintained at 160° C. and the process pressure is maintained at 289-302 psia (1992-2082 kPa) throughout the run. The selectivity to propylene oxide is 95.8 mole percent, based on moles of propylene converted. The water to propylene oxide molar ratio in the effluent stream is 4.2/1.

The gaseous effluent stream (3) from the hydro-oxidation reactor (2) is processed as shown in FIG. 1, by being fed to a first distillation column (4) containing 25 theoretical trays. Liquid propylene is obtained by condensing unconverted and make-up propylene in an external condenser (7). The liquid propylene is fed in stream 8 into the top ⅓ section of the first distillation column as liquid reflux to facilitate rectification of propylene oxide from the gaseous effluent stream. Referring to Table 1, the reflux ratio of the distillation column is provided as flow of liquid stream (8) divided by flow of gaseous stream (9) or 305.9/812.3=0.38/1. The distillation column operates at a temperature of 38° C. and a pressure of 1965 kPa at the top of the column and a temperature of 104° C. and a pressure of 1983 kPA at the bottom of the column. A liquid stream (12) is recovered from the bottom of the first distillation column (4) and fed to finishing train (column 16) for separation into a water stream (17), a purified propylene oxide stream (18), and a stream comprising primarily unconverted propylene, which in this example is recycled via line 20 to the distillation column. (Line 19 is a vent stream, which in this example is effectively zero mass balance.) The finishing column (16) contains 15 theoretical trays and operates at a temperature of 117° C. at the bottom of the column to 34° C. at the top of the column and a pressure of 188 kPa at the bottom of the column and 172 kPa at the top of the column. Table 1 sets forth mass fractions of components of input and output streams and process conditions for the above-identified example of the process invention, as referenced to FIG. 1.

The data set forth in Table 1 are obtained from an Aspen© software process simulation program available from Aspen-Technology, Inc. of Cambridge, Mass., USA, specifically, the simulator Aspen Plus version 2004.1 The program uses a property set from RK-Aspen using referenced methods from non-random two-liquid (NRTL) and steam tables. Literature data are used to determine physical properties of specific mixtures for use in models of an equation of state and activity coefficients, which are used in the simulation.

based on the total weight of the overhead stream (18). With additional purification, the recovered propylene oxide can be purified to a purity of 99 weight percent.

Example 2

With reference to FIG. 2 and Table 2, Example 1 is repeated with the exception that in place of a liquid propylene reflux, n-butane is fed to the external condenser (7) to yield a liquid butane reflux (8) for first distillation column (4), and stripper column (24) is placed between the first distillation column (4) and the finishing train (16). In the hydro-oxidation step the selectivity to propylene oxide is 96.9 mole percent, based on moles of propylene converted. The molar ratio of water to propylene oxide in the hydro-oxidation effluent stream is 4.3/1. The first hydro-oxidation effluent stream (3) is fed to first distillation column (4) using the butane rectification agent. A first overhead stream (6) comprising propylene, oxygen, hydrogen, butane, and various inert diluents, obtained from the first distillation column (4), is fed to the condenser (7) and split into a liquid butane stream (8), which is recycled to the distillation column for use as rectification agent, and a gaseous stream (9) containing unconverted propylene, oxygen, hydrogen and butane, which is recycled to the hydro-oxidation reactor. Referring to Table 2, the reflux ratio of the distillation column is calculated as flow of liquid stream (8) divided by flow of gaseous stream (9) or 313.3/495.3=0.63/1. The distillation column is operated at a temperature of 59.5° C. and a pressure of 1689 kPa at the top of the column, and a temperature of 87.5° C. and a pressure of 1707 kPa at the bottom of the column. A first bottoms stream (12) comprising water, propylene oxide, and butane, which is obtained from the first distillation column (4), is fed to the stripper column (24) to obtain therefrom an overhead stream (25) comprising primarily unconverted propylene and butane, which is recycled to the hydro-oxidation reactor (2), and a bottoms stream (26) comprising water and propylene oxide, which is fed to the finishing train (16) to obtain a purified propylene oxide (18). The stripper column (24) operates at 85.7° C. and

TABLE 1

Mass Fraction of Input and Output Streams[a]

| | Mass Fraction | | | | | | | | | | |
|---|---|---|---|---|---|---|---|---|---|---|---|
| | 1 | 3 | 5 | 6 | 8 | 9 | 11 | 12 | 17 | 18 | 20 |
| $H_2O$ | 0.0014 | 0.0137 | 0.0000 | 0.0017 | 0.0037 | 0.0009 | 0.0009 | 0.5449 | 1.0000 | 0.0123 | 0.0048 |
| $H_2$ | 0.0027 | 0.0014 | 0.0000 | 0.0010 | 0.0000 | 0.0014 | 0.0014 | 0.0000 | 0.0000 | 0.0000 | 0.0000 |
| $N_2$ | 0.0107 | 0.0107 | 0.0000 | 0.0081 | 0.0005 | 0.0108 | 0.0108 | 0.0000 | 0.0000 | 0.0000 | 0.0000 |
| $O_2$ | 0.0850 | 0.0704 | 0.0000 | 0.0537 | 0.0055 | 0.0714 | 0.0714 | 0.0000 | 0.0000 | 0.0000 | 0.0000 |
| Ar | 0.0336 | 0.0336 | 0.0000 | 0.0257 | 0.0026 | 0.0341 | 0.0341 | 0.0000 | 0.0000 | 0.0000 | 0.0000 |
| $CH_4$ | 0.0185 | 0.0185 | 0.0000 | 0.0144 | 0.0023 | 0.0188 | 0.0188 | 0.0000 | 0.0000 | 0.0000 | 0.0000 |
| $CO_2$ | 0.0112 | 0.0124 | 0.0000 | 0.0102 | 0.0037 | 0.0126 | 0.0126 | 0.0000 | 0.0000 | 0.0000 | 0.0002 |
| $C_3H_6$ | 0.8312 | 0.8233 | 0.9900 | 0.8790 | 0.9741 | 0.8442 | 0.8442 | 0.0113 | 0.0000 | 0.0007 | 0.3766 |
| $C_3H_8$ | 0.0056 | 0.0055 | 0.0100 | 0.0061 | 0.0072 | 0.0057 | 0.0057 | 0.0001 | 0.0000 | 0.0000 | 0.0023 |
| PO | 0.0001 | 0.0105 | 0.0000 | 0.0001 | 0.0002 | 0.0000 | 0.0000 | 0.4437 | 0.0000 | 0.9867 | 0.6160 |
| Total Flow Kg/sec | 824.8 | 824.8 | 6.9 | 1111.4 | 305.9 | 812.3 | 812.3 | 19.4 | 10.5 | 8.4 | 0.6 |
| Temperature K | 330.7 | 323.2 | 263.2 | 311.1 | 307.6 | 307.6 | 332.2 | 376.8 | 391.5 | 323.2 | 306.7 |
| Pressure kPa | 2096 | 1993 | 2068 | 1965 | 1965 | 1965 | 2103 | 1983 | 188 | 174 | 172 |

[a]Stream numbers are referenced with respect to FIG. 1.

The integrated process for the aforementioned process steps produces steam valued at 200 million Btu's per hour (MM Btu/h) from the hydro-oxidation process and requires 283 mM Btu/h cooling at 25° C. for the external condenser.

The propylene oxide recovered as an overhead stream (18) from the finishing column has a purity of 98.7 weight percent, 248 psia (1,707 kPa) to recover the second overhead stream (25) comprising propylene and butane, which is recycled to the hydro-oxidation process; and a second bottoms stream (26) comprising water and propylene oxide. Referring to FIG. 2, Table 2 lists mass fractions of components for input and output streams and process conditions.

TABLE 2

Mass Fractions of Components and Process Conditions for Example 2[a]

| | Mass Fraction | | | | | | | | | | |
|---|---|---|---|---|---|---|---|---|---|---|---|
| | 1 | 3 | 5 | 6 | 8 | 9 | 11 | 12 | 23 | 25 | 26 |
| $H_2O$ | 0.0020 | 0.0123 | 0.0000 | 0.0014 | 0.0023 | 0.0008 | 0.0065 | 0.0245 | 0.0000 | 0.0127 | 0.3163 |
| $H_2$ | 0.0023 | 0.0012 | 0.0000 | 0.0014 | 0.0000 | 0.0023 | 0.0012 | 0.0000 | 0.0000 | 0.0000 | 0.0000 |
| $N_2$ | 0.0086 | 0.0086 | 0.0000 | 0.0104 | 0.0005 | 0.0164 | 0.0087 | 0.0000 | 0.0000 | 0.0000 | 0.0000 |
| $O_2$ | 0.0727 | 0.0603 | 0.0000 | 0.0736 | 0.0056 | 0.1156 | 0.0610 | 0.0000 | 0.0000 | 0.0000 | 0.0000 |
| Ar | 0.0254 | 0.0254 | 0.0000 | 0.0310 | 0.0024 | 0.0487 | 0.0257 | 0.0000 | 0.0000 | 0.0000 | 0.0000 |
| $CH_4$ | 0.0145 | 0.0145 | 0.0000 | 0.0180 | 0.0021 | 0.0278 | 0.0147 | 0.0000 | 0.0000 | 0.0000 | 0.0000 |
| $CO_2$ | 0.0096 | 0.0106 | 0.0000 | 0.0139 | 0.0043 | 0.0198 | 0.0107 | 0.0005 | 0.0000 | 0.0005 | 0.0000 |
| $C_3H_6$ | 0.3401 | 0.3333 | 0.9900 | 0.4424 | 0.3689 | 0.4964 | 0.3444 | 0.1679 | 0.0000 | 0.1747 | 0.0000 |
| $C_3H_8$ | 0.0040 | 0.0039 | 0.0100 | 0.0051 | 0.0046 | 0.0055 | 0.0040 | 0.0023 | 0.0000 | 0.0024 | 0.0000 |
| PO | 0.0001 | 0.0091 | 0.0000 | 0.0004 | 0.0008 | 0.0002 | 0.0001 | 0.0186 | 0.0000 | 0.0000 | 0.4807 |
| n-Butane | 0.5208 | 0.5208 | 0.0000 | 0.4023 | 0.6084 | 0.2665 | 0.5231 | 0.7860 | 1.0000 | 0.8095 | 0.2030 |
| Total Flow Kg/sec | 949.9 | 949.9 | 6.9 | 801.5 | 313.2 | 495.3 | 939.0 | 461.6 | 0.1 | 443.7 | 17.9 |
| Temperature K | 340.8 | 323.2 | 263.2 | 332.5 | 318.4 | 318.4 | 343.2 | 360.6 | 298.2 | 358.7 | 358.7 |
| Pressure kPa | 2096 | 1993 | 2068 | 1689 | 1689 | 1689 | 2103 | 1707 | 2068 | 1707 | 1707 |

[a]Stream numbers are referenced with respect to FIG. 2.

All steam produced from the hydro-oxidation reaction is consumed in the heat exchangers (reboilers on the propylene oxide recovery columns of this process). The cooling requirement is 500 MM Btu/h at 35° C. for the external butane condenser.

The bottoms stream from the stripper column (26) is fed to finishing train (16), operating as in Example 1, for further purification and recovery of water in bottoms stream (17), propylene oxide in top stream (18), and n-butane in top stream (20). Propylene oxide from top stream (18) has a purity greater than 90 weight percent.

What is claimed is:

1. An integrated process of hydro-oxidation of an olefin to form a hydro-oxidation effluent stream comprising an olefin oxide and of separating the olefin oxide from the hydro-oxidation effluent stream, the process comprising the steps of:
   (a) contacting a reactant olefin in a gas phase in a hydro-oxidation reactor with oxygen in the presence of hydrogen and in the presence of a hydro-oxidation catalyst under reaction conditions sufficient to obtain a gas phase hydro-oxidation effluent stream comprising an olefin oxide, water, unconverted olefin, oxygen, and hydrogen;
   (b) feeding the gas phase hydro-oxidation effluent stream into a first distillation column that provides for a liquid reflux of a rectification agent in a top ⅓ section of the column;
   (c) removing from the first distillation column a first overhead stream comprising unconverted olefin, oxygen, and hydrogen, and a first bottoms stream comprising water and the olefin oxide; and
   (d) feeding the first bottoms stream comprising water and the olefin oxide into a finishing train to obtain therefrom a stream comprising the olefin oxide product.

2. The process of claim 1 wherein the rectification agent is an aliphatic hydrocarbon having a normal boiling point equal to or greater than the normal boiling point of the olefin and less than the normal boiling point of the olefin oxide.

3. The process of claim 1 wherein the rectification agent is a $C_{4-8}$ alkane or is identical to the olefin of the hydro-oxidation step.

4. The process of claim 1 wherein the olefin is propylene and the olefin oxide is propylene oxide.

5. The process of claim 1 wherein the rectification agent is propylene or butane.

6. The process of claim 1 wherein the hydro-oxidation catalyst comprises gold, silver, one or more noble metals, one or more rare earth lanthanides, or a mixture thereof, deposited on a titanium-containing support.

7. The process of claim 6 wherein the titanium-containing support comprises a porous titanosilicate.

8. The process of claim 6 wherein the catalyst further comprises one or more promoters selected from the group consisting of alkali, alkaline earth, rare earth lanthanide, and actinide elements, and mixtures thereof.

9. The process of claim 1 wherein the effluent stream from the hydro-oxidation reactor comprises from greater than 0.05 to less than 10 percent olefin oxide, from greater than 0.1 to less than 15 percent water, from greater than 1 to less than 80 percent unconverted olefin, from greater than 0.5 to less than 20 percent oxygen, from greater than 0.1 to less than 20 percent hydrogen, and from 0 to less than 70 percent diluent, by volume.

10. The process of claim 1 wherein the first distillation column comprises from 6 to 50 theoretical plates.

11. The process of claim 1 wherein the first distillation column operates at a reflux ratio from about 0.1/1 to about 10/1.

12. The process of claim 1 wherein the first distillation column operates at a bottom temperature greater than 35° C. and less than 125° C. and at a pressure greater than 50 psia (345 kPa) and less than 500 psia (3,446 kPa).

13. The process of claim 1 wherein the finishing train comprises at least one distillation column comprising from 10 to 50 theoretical plates.

14. The process of claim 1 wherein the finishing train comprises a distillation column operating at a temperature greater than −30° C. and less than 140° C. and a pressure greater than 8 psia (55 kPa) and less than 60 psia (413 kPa).

15. The integrated process of claim 1 comprising the steps of:
   (a) contacting a reactant olefin in a gas phase in a hydro-oxidation reactor with oxygen in the presence of hydrogen and in the presence of a hydro-oxidation catalyst under reaction conditions sufficient to obtain a gas phase hydro-oxidation effluent stream comprising an olefin oxide, water, unconverted olefin, oxygen, and hydrogen;

(b) feeding the gas phase hydro-oxidation effluent stream into a first distillation column that provides for a liquid phase reflux of the olefin in the top ⅓ section of the column;

(c) removing from the first distillation column a first overhead stream comprising unconverted olefin, oxygen, and hydrogen, and a first bottoms stream comprising water and the olefin oxide;

(d) feeding the first overhead stream into a condenser and withdrawing therefrom a gaseous stream comprising oxygen, hydrogen, and a portion of the unconverted olefin, and a liquid stream comprising the balance of the unconverted olefin fed to the condenser;

(e) recycling the gaseous stream from the condenser comprising oxygen, hydrogen, and a portion of the unconverted olefin to the hydro-oxidation reactor;

(f) recycling the liquid stream from the condenser comprising the balance of the unconverted olefin to the top ⅓ section of the distillation column to provide for the liquid reflux;

(g) feeding at least a portion of the bottoms stream comprising water and olefin oxide obtained from the first distillation column into a finishing train to obtain therefrom a second overhead stream comprising the olefin oxide.

16. The process of claim 15 wherein an olefin identical to the olefin reactant of the hydro-oxidation step is fed to the middle ⅓ section of the first distillation column to provide for the rectification agent.

17. The process of claim 15 wherein a portion of the first bottoms stream comprising the olefin oxide and water is fed to a reboiler from which any unconverted olefin present in the first bottoms stream is separated and recycled to the first distillation column.

18. The integrated process of claim 1 comprising the steps of:

(a) contacting in a gas phase in a hydro-oxidation reactor a reactant olefin with oxygen in the presence of hydrogen and in the presence of a hydro-oxidation catalyst under reaction conditions sufficient to obtain a gaseous hydro-oxidation effluent stream comprising an olefin oxide, water, unconverted olefin, oxygen, and hydrogen;

(b) feeding the gas phase hydro-oxidation effluent stream into a first distillation column which provides for a liquid reflux of an alkane in the upper ⅓ section of the column;

(c) removing from the first distillation column a first overhead stream comprising unconverted olefin, oxygen, hydrogen, and a portion of the alkane, and a first bottoms stream comprising water, olefin oxide, and the balance of the alkane;

(d) feeding the first overhead stream to a condenser and obtaining therefrom a gaseous stream comprising unconverted olefin, oxygen, and hydrogen, and a portion of the alkane fed to the condenser and a liquid stream comprising the balance of the alkane fed to the condenser;

(e) recycling the gaseous stream obtained from the condenser to the hydro-oxidation reactor;

(f) recycling the liquid stream obtained from the condenser to the top ⅓ section of the first distillation column;

(g) feeding the first bottoms stream comprising water, olefin oxide, and the balance of the alkane from the first distillation column to a stripper column to obtain a second overhead stream comprising the alkane and a second bottoms stream comprising water and the olefin oxide;

(h) recycling the second overhead stream comprising the alkane to the hydro-oxidation reactor and/or the first distillation column; and (i) feeding the second bottoms stream comprising water and the olefin oxide to a finishing train to obtain therefrom a third overhead stream comprising the olefin oxide.

19. The process of claim 18 wherein the reactant olefin is fed to the middle ⅓ section of the first distillation column to provide for additional reactant olefin, and the alkane is fed to the middle or top ⅓ section of the first distillation column for to provide for liquid reflux in the column.

20. The process of claim 18 wherein a portion of the first bottoms stream comprising the olefin oxide, water, and a portion of the alkane is fed to a reboiler from which any unconverted olefin and alkane present in the first bottoms stream is separated and then recycled to the first distillation column.

* * * * *